United States Patent [19]

Okauchi et al.

[11] 4,324,795
[45] Apr. 13, 1982

[54] ACARICIDAL AGENTS

[75] Inventors: Tetsuo Okauchi, Hirakata; Kentaro Hiraga, Nagaokakyo; Yasuo Sato, Kyoto, all of Japan

[73] Assignee: Takeda Chemical Industries, Ltd., Japan

[21] Appl. No.: 190,412

[22] Filed: Sep. 24, 1980

[30] Foreign Application Priority Data

Sep. 25, 1979 [JP] Japan .................. 54-123432

[51] Int. Cl.$^3$ ............................................ A01N 43/36
[52] U.S. Cl. .................................................... 424/274
[58] Field of Search ..................... 424/274; 260/326.9

[56] References Cited

U.S. PATENT DOCUMENTS 4,046,753  9/1977  Fisher et al. ................... 260/158

OTHER PUBLICATIONS

Derwent Abstract (35571S-B) of German Offenlegungsschrift 1957783; 5/19/71.

Current Abstracts of Chemistry & Index Chemicus, 1-14-70, vol. 36(2), Issue 320, Abstract 126803.

Primary Examiner—Leonard Schenkman
Attorney, Agent, or Firm—Wenderoth, Lind & Ponack

[57] ABSTRACT

Novel acaricidal agents which contains, as an active ingredient, a pyrroline derivative of the formula:

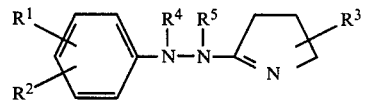

wherein
$R^1$ and $R^2$ are each hydrogen, halogen or lower alkyl;
$R^3$ is hydrogen or phenyl which may be substituted with halogen;
$R^4$ is hydrogen or lower alkanoyl and $R^5$ is hydrogen or phenyl or its acid addition salt and a carrier, vehicle or diluent thereof, can effectively eradicate ticks and mites.

11 Claims, No Drawings

ACARICIDAL AGENTS

The present invention relates to novel acaricidal agents.

Ticks and mites which are parasitic on a variety of garden plants and domesticated animals have short life cycles and very high breeding capabilities. These characteristics demand a frequent application of control chemicals, which fosters in turn their readiness to acquire the resistance to such chemicals. It is for this reason that the efficacies of many of the control chemicals hitherto employed tend to diminish by degrees and that, accordingly, it has been desired to develop new control chemicals. Referring to the characteristic features that are particularly required of acaricidal agents, in view of the exceedingly high breeding capabilities of ticks and mites, such acaricidal agents will not only have to possess the acaricidal action but also develop the breeding suppressing activities such as egglaying inhibiting action and ovicidal property.

Under these circumstances, the present inventors, after the extensive screening work on a wide variety of chemicals for their acaricidal activities, found out that particular pyrroline compounds exhibited extremely potent controlling effect against ticks and mites, when applied on their body surfaces, hosts, etc. The finding was followed by further studies, which have culminated in the present invention.

Thus, the present invention relates to an acaricidal agent which contains, as an active ingredient, at least one member of the class of the compounds represented by the formula (I):

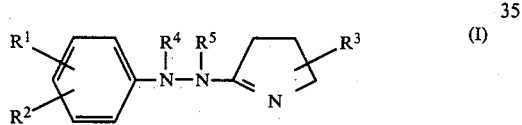

wherein $R^1$ and $R^2$ are each hydrogen, halogen or lower (especially $C_{1-3}$) alkyl; $R^3$ is hydrogen or phenyl which may be substituted by halogen; $R^4$ is hydrogen or lower (especially $C_{2-4}$) alkanoyl; $R^5$ is hydrogen or phenyl, or their acid addition salts.

Among the above-mentioned compounds (I), preferable compounds are those of the formula (II):

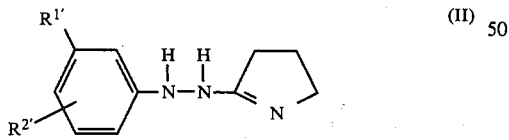

wherein $R^{1'}$ is halogen and $R^{2'}$ is hydrogen, halogen or $C_{1-3}$ alkyl or their acid addition salt, which are novel compounds.

The compounds represented by the above general formula (I) display the extremely high control activity against a variety of bloodsucking ticks living on domestic animals such as cattle, horses, goats and sheep, and poultry such as barn-door fowls and turkeys, and against the so-called leaf-mites that live and feed on fruit-bearing trees such as apple, pear, orange and peach, various legumes, vegetables such as egg plant and cucumber, specialty crops such as hop, mulberry and tobacco, and ornamental flowers such as carnation and tulip, when such compounds are used for treatment of such parasite bodies or their hosts by spray, etc.

These compounds not only possess the acaricidal activity but also inhibit the oviposition of acari at lowered concentrations. More surprisingly, these compounds when applied to ticks not only exhibit the effect of inhibiting the blood-sucking act against ticks not having sucked the blood, but also block the blood-sucking behavior against ticks gorging on the blood of animals and detach them from the hosts, thereby causing them to die of incomplete growth. These compounds are also safe to man and easy to handle.

The followings are examples of the compounds represented by the formula (I). As shown herein by way of example, these compounds may be put into use as acid addition salts or in the form of free base. As examples of such acid addition salts, there may be mentioned inorganic acid salts such as hydrochlorides, sulfates, nitrates, etc., and organic acid salts such as p-toluenesulfonates, maleates, tartarates and oxalates.

TABLE 1

| Compound No. | Chemical Name |
| --- | --- |
| 1 | 2-[N'-(2-chlorophenylhydrazino)]-1-pyrroline hydrochloride |
| 2 | 2-[N'-(2-methylphenylhydrazino)]-1-pyrroline hydrochloride |
| 3 | 2-[N'-(4-chlorophenylhydrazino]-1-pyrroline hydrochloride |
| 4 | 2-[N'-(4-methylphenylhydrazino)]-1-pyrroline hydrochloride |
| 5 | 2-[N'-(4-bromophenylhydrazino)]-1-pyrroline hydrochloride |
| 6 | 2-(N'-phenylhydrazino)-4-phenyl-1-pyrroline hydrochloride |
| 7 | 2-(N'-phenylhydrazino)-4-(4-chlorophenyl)-1-pyrroline hydrochloride |
| 8 | 2-(N'-phenylhydrazino)-1-pyrroline hydrochloride |
| 9 | 2-(N,N'-diphenylhydrazino)-1-pyrroline |
| 10 | 2-(N,N'-diphenyl-N'-propionylhydrazino)-1-pyrroline hydrochloride |
| 11 | 2-[N'-(2,3-dichlorophenylhydrazino)]-1-pyrroline hydrochloride |
| 12 | 2-[N'-(3-chloro-2-methylphenylhydrazino)]-1-pyrroline hydrochloride |
| 13 | 2-[N'-(2,4-dichlorophenylhydrazino)]-1-pyrroline hydrochloride |
| 14 | 2-[N'-(4-chloro-2-methylphenylhydrazino)]-1-pyrroline hydrochloride |
| 15 | 2-[N'-(3-fluorophenylhydrazino)]-1-pyrroline hydrochloride |
| 16 | 2-[N'-(2-fluorophenylhydrazino)]-1-pyrroline hydrochloride |
| 17 | 2-[N'-(4-chloro-2-fluorophenylhydrazino)]-1-pyrroline hydrochloride |
| 18 | 2-[N'-(3-chlorophenylhydrazino)]-1-pyrroline hydrochloride |
| 19 | 2-[N'-(2-methylphenylhydrazino)]-4-(4-chlorophenyl)-1-pyrroline hydrochloride |
| 20 | 2-[N'-(2-bromophenylhydrazino)]-1-pyrroline hydrochloride |
| 21 | 2-[N'-(3-bromophenylhydrazino)]-1-pyrroline hydrochloride |
| 22 | 2-[N'-(2,5-dichlorophenylhydrazino)]-1-pyrroline hydrochloride |
| 23 | 2-[N'-(2,6-dichlorophenylhydrazino)]-1-pyrroline hydrochloride |
| 24 | 2-[N'-(3,4-dichlorophenylhydrazino)]-1-pyrroline hydrochloride |
| 25 | 2-[N'-(3,5-dichlorophenylhydrazino)]-1-pyrroline hydrochloride |
| 26 | 2-[N'-(2,4-difluorophenylhydrazino)]-1-pyrroline hydrochloride |
| 27 | 2-[N'-(2,6-difluorophenylhydrazino)]-1-pyrroline hydrochloride |
| 28 | 2-[N'-(2,4-dibromophenylhydrazino)]-1-pyrroline hydrochloride |

TABLE 1-continued

| Compound No. | Chemical Name |
|---|---|
| 29 | 2-[N'-(2,5-dibromophenylhydrazino)]-1-pyrroline hydrochloride |
| 30 | 2-[N'-(2,6-dibromophenylhydrazino)]-1-pyrroline hydrochloride |

The compounds of the formula (I) may be easily synthesized in the manner shown in the following production examples or, for example, by the procedures described in West-German Published Unexamined Patent Application No. 1957783 and Bull. Soc. Chim. Fr., 3704 (1969).

PRODUCTION EXAMPLE 1

Synthesis of
2-[N'-(3-Chlorophenylhydrazino)]-1-Pyrroline Hydrochloride

In 5 ml of benzene was dissolved 2 g of 2-pyrrolidinone, and a solution of 1.5 g of phosphorus oxychloride in 3 ml of benzene was added dropwise to the solution with stirring under ice-cooling over a 10-minute period. After the dropwise addition was concluded, the solution was stirred at room temperature for 3 hours, followed by adding 4.5 g of 3-chlorophenylhydrazine sulfate and warming at 65° C. for 3 hours. After cooling, the separated benzene layer was removed by decantation, and to the residue was added 50 ml of water and the PH of the mixture was adjusted to 10 with 1 N-NaOH and the mixture was extracted with three 50 ml portions of ethyl acetate. The ethyl acetate layer was washed with water, dried over anhydrous sodium sulfate, and concentrated under reduced pressure to yield 3.5 g of an oily material. The material was dissolved in 10 ml of ethanol and followed by addition of 2 ml of a 2 N HCl-ether solution to afford instantaneously crystals of 2-[N'-(3-chlorophenylhydrazino)]-1-pyrroline hydrochloride. The resulting crystals were collected by filtration and recrystallized from methanol-ether to yield 2.8 g of crystals. m.p., 242–243° C.

Elementary analysis for $C_{10}H_{12}N_3 \cdot HCl$: Calcd., C 48.80; H 5.32; N 17.07. Found, C 48.91; H 5.42; N 17.21.

Among the compounds obtained thus, physicochemical data of the new compounds are tabulated in Table 2.

TABLE 2

| Compound No. | M.P. (°C.) | Molecular formula | Elementary analysis (%) Theoretical values are in parentheses | | |
|---|---|---|---|---|---|
| | | | C | H | N |
| 2 | 258–262 | $C_{11}H_{15}N_3 \cdot HCl$ | 58.75 (58.53) | 7.28 (7.15) | 18.65 (18.62) |
| 4 | 260–263 | $C_{11}H_{15}N_3 \cdot HCl$ | 58.61 (58.53) | 7.24 (7.15) | 18.69 (18.62) |
| 6 | 240–245 | $C_{16}H_{17}N_3 \cdot HCl$ | 66.63 (66.77) | 6.11 (6.30) | 15.06 (14.60) |
| 7 | 245–250 | $C_{16}H_{16}N_3Cl \cdot HCl$ | 59.31 (59.60) | 5.27 (5.32) | 13.44 (13.04) |
| 9 | 139–140 | $C_{16}H_{17}N_3$ | 76.19 (76.46) | 6.70 (6.82) | 16.50 (16.72) |
| 10 | 217–221 | $C_{19}H_{21}N_3O \cdot HCl \cdot \frac{1}{2} H_2O$ | 64.42 (64.66) | 6.63 (6.57) | 11.74 (11.91) |
| 11 | 274–277 | $C_{10}H_{11}N_3Cl_2 \cdot HCl$ | 42.50 (42.78) | 4.33 (4.28) | 14.88 (14.97) |
| 12 | 158–162 | $C_{11}H_{14}N_3Cl \cdot HCl$ | 49.55 (50.76) | 5.43 (5.77) | 15.75 (16.15) |
| 13 | 272–277 | $C_{10}H_{11}N_3Cl_2 \cdot HCl$ | 42.75 (42.78) | 4.31 (4.28) | 15.06 (14.97) |
| 14 | 273–278 | $C_{11}H_{14}N_3Cl \cdot HCl$ | 50.71 | 5.81 | 16.16 |
| | | | (50.76) | (5.77) | (16.15) |
| 15 | 265–275 | $C_{10}H_{12}N_3F \cdot HCl$ | 52.26 (52.28) | 5.67 (5.72) | 18.23 (18.30) |
| 16 | 241–243 | $C_{10}H_{12}N_3F \cdot HCl$ | 51.95 (52.28) | 5.67 (5.72) | 18.19 (18.30) |
| 17 | 263–266 | $C_{10}H_{11}N_3FCl \cdot HCl$ | 45.39 (45.47) | 4.33 (4.59) | 15.80 (15.91) |
| 18 | 242–243 | $C_{10}H_{12}N_3Cl \cdot HCl$ | 48.91 (48.80) | 5.42 (5.32) | 17.21 (17.07) |
| 19 | 257–260 | $C_{17}H_{18}N_3Cl \cdot HCl$ | 60.28 (60.72) | 5.57 (5.69) | 12.53 (12.50) |

Given below are examples of the experiment on the controlling effects of the representative compounds (I).

EXPERIMENT EXAMPLE 1

Egg-laying Inhibitory Activity Upon Completely Engorged (Blood Saturated) Female Adults of *Haemaphysalis longicornis*

A suitable amount of each of the compounds indicated in Table 3 was dissolved in methanol to prepare a test solution of the desired application concentration.

By means of a micropipet, this test solution was applied by dropping onto a group composed for each concentration of five or ten female adults of *Haemaphysalis longicornis* immediately after having gorged fully on the blood and dropped off from the host at the rate of 5 μl per each group. After the solvent has been air-dried, the ticks were transferred to a dish and held in a constant-temperature, constant-humidity chamber at 25° C. and 95% R.H. for 3 weeks. Then, the egg-laying inhibition effect of each compound was determined by comparing the weight of eggs laid by the ticks treated with 30 μg and 300 μg of the compound per body weight (gram) respectively with the weight of eggs laid by control ticks treated with the solvent alone and by calculating the egg-laying inhibition rate according to the equation given below. That is to say, 100% of the egg-laying inhibition rate means that no egg was laid, while 0% means that there took place the egg-laying equal to the control reference.

Egg-laying inhibition rate $(\%) = 100 - W/W_o \times 100$ where;
W = the weight of eggs laid by treated ticks
$W_o$ = the weight of eggs laid by control ticks

TABLE 3

Egg-laying inhibitory activity upon completely engorged (blood saturated) female adults of *Haemaphysalis longicornis* (the egg-laying inhibition rates found when treated with 300 μg and 30 μg of compound per gram body weight, respectively, %)

| Compound No. | Egg-laying inhibition rate (%) (treatment concentration) | |
|---|---|---|
| | 300 μg/g | 30 μg/g |
| 1 | 100 | 68 |
| 2 | 93 | 16 |
| 3 | 32 | 0 |
| 4 | 20 | 0 |
| 5 | 13 | 0 |
| 8 | 100 | 82 |
| 9 | 46 | 7 |
| 11 | 100 | 100 |
| 12 | 100 | 67 |

TABLE 3-continued

Egg-laying inhibitory activity upon completely engorged (blood saturated) female adults of *Haemaphysalis longicornis* (the egg-laying inhibition rates found when treated with 300 μg and 30 μg of compound per gram body weight, respectively, %)

| Compound No. | Egg-laying inhibition rate (%) (treatment concentration) | |
|---|---|---|
| | 300 μg/g | 30 μg/g |
| 13 | 100 | 19 |
| 15 | 100 | 84 |
| 16 | 100 | 66 |
| 17 | 89 | 29 |
| 18 | 100 | 90 |

EXPERIMENT EXAMPLE 2

Blood-sucking Inhibitory Activity Upon Female Adult Ticks While Engorging

A suitable amount of each of the compounds indicated in Table 4 was dissolved in methanol to prepare a test solution of the desired application concentration. About 50 unengorged adults of *Haemaphysalis longicornis* were deposited on the auricles of a rabbit for each test solution and, after it was confirmed that they had attached properly to the host and were gorging on the blood three days later, each of the above test solutions was sprayed by means of a small-sized sprayer at the rate of 3 ml per ear.

For the control experiment, fenitrothion, an organophosphorus insecticidal and acaricidal agent, was dissolved in methanol to the desired concentration to spray in the same manner as the test solution. Over four days after spraying, the number of ticks remaining attached to the hosts was investigated for each group of the experiments inclusive of the control experiment, and the blood-sucking inhibition effect of each compound was compared by determining the blood-sucking inhibition rate as calculated according to the equation given below:

Blood-sucking inhibition rate $(\%) = (q_o - q)/q_o \times 100$ where;
$q_o$ = ratio of ticks attached in non-treated control experiment
$q$ = ratio of ticks attached in a treated experiment

TABLE 4

| Blood-sucking inhibitory effect upon female adult ticks while engorging | | |
|---|---|---|
| Compound No. | Blood-sucking inhibition rate up to 4 days after spraying, (%) (treatment concentration) | |
| | 1000 ppm | 3000 ppm |
| 1 | 78 | 100 |
| 11 | 98 | 100 |
| 18 | 100 | 100 |
| Control chemical (fenitrothion) | 0 | 35 |

EXPERIMENT EXAMPLE 3

Acaricidal Action Upon Unengorged Larval Ticks

A suitable amount of each of the compounds indicated in Table 5 was dissolved in methanol to prepare a test solution of the desired application concentration. Each test solution was dropped in the filter-paper side of a bag (which comprised of a Toyo filter paper No. 2 manufactured by Toyo filter paper Ltd., Japan of 5×5 cm in size heat-sealed with a 0.1 mm thick, clear polyethylene film) and, after the solvent had been air-dried, about 100 unengorged larvae of *Haemaphysalis longicornis* two to four weeks after hatching from eggs were placed in the bag, followed by sealing it. 0.4 ml of water was dropped on the filter-paper side for the purpose of prevention of drying, and the bag was transferred to a dish of 7 cm in diameter and protected under the conditions of 25° C. and 95% R.H. 14 days later, the filter paper bag was taken out of the dish, and the number of dead ticks was investigated to calculate the $LC_{50}$ (50% lethal concentration) according to the probit method by BLISS.

TABLE 5

| Acaricidal effect upon unengorged larval ticks. | |
|---|---|
| Compound No. | 50% lethal concentration (ppm) |
| 1 | 18.3 |
| 11 | 9.83 |
| 18 | 6.38 |

EXPERIMENT EXAMPLE 4

Control Effect Upon Leaf-Mites

Female adults of *Tetranychus urticae* were allowed to feed on the seedlings of kidney bean (first leaf-unfolding stage), water cultured in a polyethylene cup of 6 cm diameter, a seedling per cup, at a rate of 10 mites per cup, and 20 ml of water containing 500 ppm of each of the compounds shown in Table 6 was sprayed to them on the following day by means of a spraying apparatus held at a distance of about 80 cm from each cup. The treated plants were held in a greenhouse of 28° C., and the number of survived mites were counted two days later. The test was repeated three times, and the average percent decrease was calculated by the following equation:

$$\text{Average percent decrease} = 100 \times \left(1 - \frac{\text{No. of mites attached after spray}}{\text{No. of mites attached before spray}}\right)$$

The results are shown in Table 6, whereby the acaricidal activity of 0 means that the average percent decrease of mites was not more than 20%; the activity of 1 means that the average percent decrease of mites was within the range of 21 to 50%; the activity of 2 means that the average percent decrease was in the range of 51 to 89%; and the activity of 3 means the average percent decrease of not less than 90%.

TABLE 6

| Acaricidal activity upon leaf-mites | | | |
|---|---|---|---|
| Compound No. | Acaricidal activity | Compound No. | Acaricidal activity |
| 1 | 3 | 11 | 3 |
| 2 | 3 | 12 | 3 |
| 3 | 3 | 13 | 3 |
| 4 | 3 | 14 | 2 |
| 5 | 3 | 15 | 2 |
| 6 | 1 | 16 | 3 |
| 7 | 1 | 17 | 3 |
| 8 | — | 18 | 3 |
| 9 | 1 | 19 | 2 |
| 10 | 3 | Control | 0 |

TABLE 6-continued

| Acaricidal activity upon leaf-mites | | | |
|---|---|---|---|
| Compound No. | Acaricidal activity | Compound No. | Acaricidal activity |
| | (water) | | |

Remarks:
the symbol, "—", means that no test was performed.

In putting into actual use the compounds of the formula (I), each of them may be employed as it is but normally it is previously admixed with a suitable vehicle or adjuvant and processed into such application forms as powder, microgranules, solution, emulsifiable concentrate and wettable powder, so as to apply these forms or dilute them with water or a suitable organic solvent (e.g., tetrahydrofuran, dimethylsulfoxide, acetone, methanol, ethanol, machine oil, etc.). Examples of the emulsifying or dispersing agents being usable may include nonionic substances such as the condensation products of ethylene oxide with aliphatic alcohols, amines or carboxylic acids having long-chain hydrocarbon groups of 10 to 20 carbon atoms, e.g. the condensate of octadecyl alcohol with 25 to 30 mole equivalents of ethylene oxide or the commercially available condensate of oleylamine with 12 mole equivalents of ethylene oxide or the condensate of dodecylmercaptan with 12 mole equivalents of ethylene oxide; anionic emulsifiers such as the sodium salt of dodecyl alcohol sulfate, the sodium salt of dodecylbenzene sulfonate, the potassium or triethanolamine salt of oleic acid or abietic acid or their mixture and the sodium salts of petroleum-based sulfonic acids; and cationic substances such as cetyl pyridinium bromide and dihydroxyethylbenzyldodecylammonium chloride. These premixed composition for diluted solution or diluted mixture are usually formed at a concentration of 5% to 70% W/W.

As to the vehicles or carriers for dusts and microgranules, there may be mentioned, for example, substances of mineral origin such as talc, kaoline, bentonite, powdered silica and calcium phosphate, and substances of biological origin such as lactose, cork powder and wood meal.

If necessary, fatty acids, casein or alginates, etc. may be further added so as to improve the dispersability, adhesiveness or penetration.

The present acaricidal agent may be employed in mixture or conjunction with other suitable agricultural chemicals, disinfectants, detergents and so forth, unless they deteriorate its effect. For example, by using the acaricidal agent in admixture or as a mixed formulation with various organophosphorus insecticides or carbamate based insecticides, or a variety of fungicides and bactericides, one can realize the improved control effects or labor-savings in the control work through the synergism to be developed therefrom.

The present acaricidal agent is used by dusting or spraying it inside or outside the breeding buildings for domestic animals and poultry intended to be cared for, or by bathing or immersing their bodies in it. In addition, the acaricidal agent is dusted over ranches, orchards, flower gardens, vegetable farms, etc. The application rate varies with the form of preparations, application method, species or kinds or sizes of useful animals and plants, species and breeding extent of acari, environmental factors, etc., and, in applying it directly to the bodies of animals in the form of a solution by a bathing or spraying method, it is desirable to use a diluted solution of 0.001% to 5% W/W (10 to 50,000 ppm) preferably 0.005% to 0.5% W/W (50 to 5,000 ppm). And, in applying it in a form of dust, it is desirable to use at a concentration of 0.1% to 30% W/W, preferably 0.5% to 5% W/W. In cases in which dusts, solution, etc. are applied in ranches or quarters inside or outside breeding buildings, further, it is dusted directly as it is or after being suitably diluted at the application rate of 5 to 250 g per 10 a. When dusts, aqueous solution, solutions, etc. are applied onto fruit trees, vegetables, specialty crops, ornamental flowers, etc., moreover, the acaricidal agent is dusted or sprayed directly onto them or applied for soil treatment, as it is or after being suitably diluted, at the application rate of 10 to 300 g per 10 a so as to achieve the exceedingly high control effects.

Below given are some examples of the present acaricidal agent, which are not intended to limit the scope of the present invention.

EXAMPLE 1

Wettable Powder

| | |
|---|---|
| 2-[N'-(2-chlorophenylhydrazino)]-1-pyrroline hydrochloride | 50 parts |
| Neogen (produced by Dai-ichi Kogyo Seiyaku Co., Ltd., Japan | 5 parts |
| Phosphoric acid | 0.5 part |
| Kaoline | 44.5 parts |

The above ingredients were mixed and pulverized to produce a wettable powder.

EXAMPLE 2

Dusts

| | |
|---|---|
| 2-[N'-(3-chlorophenylhydrazino)]-1-pyrroline hydrochloride | 2 parts |
| Highly dispersable silicic acid | 1 part |
| Kaoline | 97 parts |

The above ingredients were mixed and pulverized to prepare dusts.

EXAMPLE 3

Soluble Powder

| | |
|---|---|
| 2-(N'-phenylhydrazino)-1-pyrroline hydrochloride | 50 parts |
| Neogen (produced by Dai-ichi Kogyo Seiyaku Co., Ltd., Japan) | 5 parts |
| Lactose | 45 parts |

The above ingredients were mixed and pulverized to obtain a soluble powder.

EXAMPLE 4

Solution

| | |
|---|---|
| 2-[N'-(3-chlorophenylhydrazino)]-1-pyrroline hydrochloride | 10 parts |
| Neogen (produced by Dai-ichi Kogyo Seiyaku Co., Ltd., Japan) | 5 parts |
| Eriogreen B-400 (produced by Sumitomo Chemical Co., Ltd., Japan) | 0.01 part |

The above ingredients were mixed and dissolved in 84.99 parts of water to obtain a solution.

EXAMPLE 5

Emulsion

| | |
|---|---|
| 2-[N'-(2,3-dichlorophenylhydrazino)]-1-pyrroline | 10 parts |
| Nonipol (produced by Sanyo Chemical Industries, Ltd., Japan) | 20 parts |
| Xylene | 70 parts |

The above ingredients were mixed to obtain an emulsion.

What is claimed is:

1. A method of eradicating ticks or mites which comprises bringing them into contact with an effective amount of a compound of the formula:

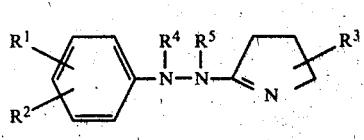

wherein
R$^1$ and R$^2$ are each hydrogen, halogen or lower alkyl;
R$^3$ is hydrogen or phenyl which may be substituted with halogen;
R$^4$ is hydrogen or lower alkanoyl and R$^5$ is hydrogen or phenyl or its acid addition salt.

2. The method according to claim 1, wherein ticks or mites are bloodsucking ticks living on domestic animals.

3. The method according to claim 2, wherein ticks are brought into contact with the compound in the form of solution by bathing or spraying.

4. The method according to claim 3, wherein the content of the compound is 0.001% to 5% (W/W) in the solution.

5. The method according to claim 1, wherein ticks or mites are leaf-mites.

6. The method according to claim 1, wherein R$^1$ and R$^2$ are each halogen.

7. The method according to claim 1, wherein R$^1$ is halogen and R$^2$ is hydrogen.

8. The method according to claim 1, said compound being 2-[N'-(2-chlorophenylhydrazino)]-1-pyrroline hydrochloride.

9. The method according to claim 1, said compound being 2-[N'-(2,3-dichlorophenylhydrazino)]-1-pyrroline hydrochloride.

10. The method according to claim 1, said compound being 2-[N'-(3-chlorophenylhydrazino)]-1-pyrroline hydrochloride.

11. The method according to claim 1, said compound being 2-(N'-phenylhydrazino)-1-pyrroline hydrochloride.

* * * * *